United States Patent [19]
Flick

[11] Patent Number: 5,957,872
[45] Date of Patent: Sep. 28, 1999

[54] HEEL CARE DEVICE AND METHOD

[75] Inventor: Roland E. Flick, Elma, N.Y.

[73] Assignee: Gaymar Industries, Inc., Orchard Park, N.Y.

[21] Appl. No.: 09/144,703

[22] Filed: Sep. 1, 1998

Related U.S. Application Data

[60] Provisional application No. 60/057,817, Sep. 4, 1997.

[51] Int. Cl.⁶ ...................................................... A61F 5/00
[52] U.S. Cl. .............................. 602/13; 128/869; 128/882
[58] Field of Search ..................................... 128/845, 846, 128/869, 882; 602/13, 23, 27

[56]   References Cited

U.S. PATENT DOCUMENTS

| | | | |
|---|---|---|---|
| 3,345,654 | 10/1967 | Noble | 5/319 |
| 3,351,055 | 11/1967 | Gottfried | 602/13 |
| 4,266,298 | 5/1981 | Graziano | 2/22 |
| 4,730,610 | 3/1988 | Graebe | 128/882 |
| 5,020,523 | 6/1991 | Bodine | 128/80 R |
| 5,328,445 | 7/1994 | Spahn et al. | 602/13 |
| 5,372,576 | 12/1994 | Hicks | 602/27 |
| 5,389,065 | 2/1995 | Johnson, Jr. | 602/27 |
| 5,460,600 | 10/1995 | Bieling | 128/882 |
| 5,489,259 | 2/1996 | Jacobs et al. | 602/13 |
| 5,571,077 | 11/1996 | Klearman | 128/882 |
| 5,577,998 | 11/1996 | Johnson | 128/882 |
| 5,603,690 | 2/1997 | Barry | 601/148 |
| 5,613,941 | 3/1997 | Prengler | 602/13 |
| 5,833,639 | 11/1998 | Nunes | 602/13 |

*Primary Examiner*—Michael A. Brown
*Attorney, Agent, or Firm*—Hodgson, Russ, Andrews, Woods & Goodyear LLP

[57]   ABSTRACT

The present invention is a protective and pressure normalizing device for a body extremity, that has a topside, an underside and two other sides. The device has an inflatable member, a non-inflatable member, a heel aperture, releasable securing means and a nozzle. The inflatable member has a lower portion, an intermediate portion, and an upper portion. Each portion contacts at least a portion of the other sides of the respective lower, intermediate, and upper region of the extremity. The heel aperture exposes the underside of the intermediate region. The non-inflatable member contacts at least a portion of the underside of the lower region. The inflatable member and heel aperture surround at least a portion of the non-inflatable member. The releasable securing means secures the device at least about the lower portion. The device engages and partially encloses in a cradling fashion the extremity. Thereby, the inflating member applies a uniform interface pressure where it is applied to the extremity.

22 Claims, 6 Drawing Sheets

HEEL CARE DEVICE AND METHOD

The present application relies on the priority of U.S. Provisional Patent Application Ser. No. 60/057,817 (filed Sep. 4, 1997).

FIELD OF THE INVENTION

The present invention generally relates to devices and methods for stabilizing and supporting the foot, in particular the heel, of a human body. The invention, more specifically, is an inflatable device that provides protection for, and relieves pressure on the foot, and particularly the heel area of the foot, when the body is in a supine position.

BACKGROUND OF THE INVENTION

U.S. Pat. No. 5,489,259 to Jacobs et al. relates to a pressure-normalizing single-chambered static pressure device for supporting and protecting a body extremity, in particular a heel. That device has an inflatable member, a plurality of seams, and apertures along those seams. Those plurality of seams, according to Jacobs et al., "enhance the ability of that device to produce a cradling effect whereby [the] interior surface [of that device] can better engage and fully conform to the contour of the lower extremity." Col 7, lines 6–9 (brackets added for clarity and deleted numbers.) Thus, without those seams that device, according to Jacobs et al., would not adequately cradle the extremity. Those seams are also interspaced throughout that device and contact each aperture. As such, the inflated or deflating air must circumvent the maze of apertures and seams to inflate or deflate. Such a maze could inhibit the inflation member from attaining an uniform interface pressure.

The present invention solves these problems.

SUMMARY OF THE INVENTION

The present invention is a protective and pressure normalizing device for a body extremity, that has a topside, an underside and two other sides. The device has an inflatable member, a non-inflatable member, a heel aperture, releasable securing means and a nozzle. The inflatable member has a lower portion, an intermediate portion, and an upper portion. Each portion contacts at least a portion of the other sides of the respective lower, intermediate, and upper region of the extremity. The heel aperture exposes the underside of the intermediate region. The non-inflatable member contacts at least a portion of the underside of the lower region. The inflatable member and heel aperture surround at least a portion of the non-inflatable member. The releasable securing means secures the device at least about the lower portion. The device engages and partially encloses in a cradling fashion the extremity. Thereby, the inflating member applies a uniform interface pressure where it is applied to the extremity.

It is an object of the present invention to provide a device and method for stabilizing the ankle while relieving pressure on the heel of the foot, and while protecting the toe area from contact with external objects.

A further object of the present invention is to provide a device and method for supporting and stabilizing the ankle and heel of the foot in order to prevent shortening of the Achilles tendon, i.e., "foot drop".

A further object of the present invention is to provide a device and method for supporting and stabilizing the ankle while relieving pressure on the heel which is adaptable to fit different sized feet and can be worn on either the left or right foot.

A further object of the present invention is to minimize pressure contact between the heel and the surface of a hospital bed, thereby decreasing the risk to the patient of the formation of decubitus ulcers on the heel area as a result of such contact.

A further object of the present invention is to limit contact between the foot of a patient, especially the toe area of the foot, and objects in the patient's surroundings such as sheets, blankets etc.

It is a further object of the present invention to provide an inflatable device for surrounding an ankle and which is provided with means for preventing the ankle from rotating with respect to the leg once the device has been inflated.

It is a further object of the present invention to provide a foot care device which is of simple construction and of a design which is simple and inexpensive to manufacture.

It is a further object of the invention to provide a foot care device which holds the foot securely in the desired position and which supports the foot in a manner which prevents the foot from slipping within the device.

BRIEF DESCRIPTION OF THE DRAWINGS

For a further understanding of the invention, as well as its characterizing features, reference should now be made to the accompanying drawings wherein.

DETAILED DESCRIPTION OF THE PRESENT INVENTION

Figure 1:
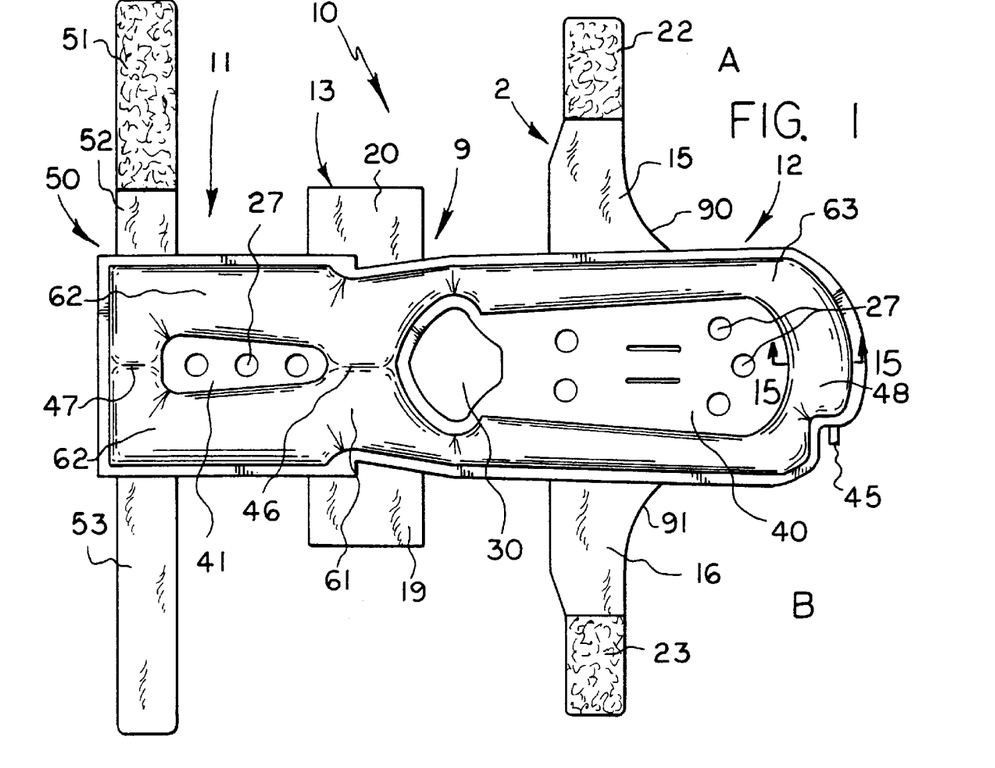
FIG. 1 is a top plan view of the foot care device of the present invention.

FIG. 1 shows a top plan view of a foot care device 10 according to the present invention. Foot care device 10 may be constructed of a lightweight cotton, gauze, paper or synthetic material which may be woven or non-woven material, or any other material which is breathable and suitable for use in a hospital, alternative care or home care environment. The material must be strong enough to be secured about the foot and leg of a patient, and capable of being comfortably placed in contact with the foot, ankle and leg of a patient. The selected material should minimize shear force on the patient's tissue and should provide adequate wicking characteristics such that moisture is drawn away from the skin of the lower leg and foot, keeping the foot and leg at a normal temperature. Further the material must be one of sufficient flexibility and pliability to conform readily to the shape of the patient's foot.

As further described below, certain portions of the selected material must be sealed such that an inflatable interior channel means may be formed within the device, and whereby the inflatable interior channel means may be inflated and air pressure may be maintained within the channel means.

Foot care device 10 comprises three interconnected and cooperating sections as major components: foot section 12, ankle section 9 and leg section 11. An inflatable interior channel 48 extends throughout these three sections.

Inflatable interior channel means 48 is configured to form one or more air cushions which provide support to a patient's foot, ankle, or leg. (Best illustrated in FIGS. 3 and 4.) In other words, inflation of interior channel means 48 inflates foot cushioning portion 63, ankle support portion 61, and leg cushioning portion 62 of device 10 so as to form a soft, flexible supporting cushion around the lower leg, toe, and ankle areas of a patient's foot. Inflatable interior channel means 48 is constructed so as to readily conform to the anatomy of the foot of a patient in such a manner as to hold the foot securely and comfortably in a position which minimizes pressure on the heel. In this manner, formation of decubitus ulcers on the heel are substantially prevented.

In a preferred embodiment inflatable interior channel means 48 interconnects foot section 12, ankle section 9 and leg section 11, and forms foot cushioning portion 63, ankle support portion 61 and leg cushioning portion 62 such that all three cushioning portions can be inflated through nozzle 45. In use, inflatable interior channel means 48 is inflated through nozzle 45, which may include a check valve, to a pressure which provides the desired support and comfort to a patient. Alternative embodiments may have different inflating configurations yet still remain within the scope of the present invention.

Foot cushioning portion 63 is preferably positioned to extend outwardly of the device past the toes of a patient such that contact between the patient's toes and objects in the patient's immediate vicinity, e.g., sheets and blankets of a hospital bed, is substantially prevented. In addition to foot cushioning portion 63, foot section 12 includes one or more foot strap means 2, a recessed foot portion 40, and in addition, partially includes heel opening 30. Recessed foot portion 40, non-inflated, may be provided with means 27, aperture, for exchanging air between the foot of a patient and the surrounding atmosphere. Foot strap means 2 includes two elongated tabs, 15 and 16, one tab extending from each side of device 10. For convenience, the sides of device 10 are referred to herein as side A and side B, and are indicated in the drawing figures as A and B. For example, elongated tab 15 is located on side A of device 10 and elongated tab 16 is located on side B of device 10.

Figures 3, 4:
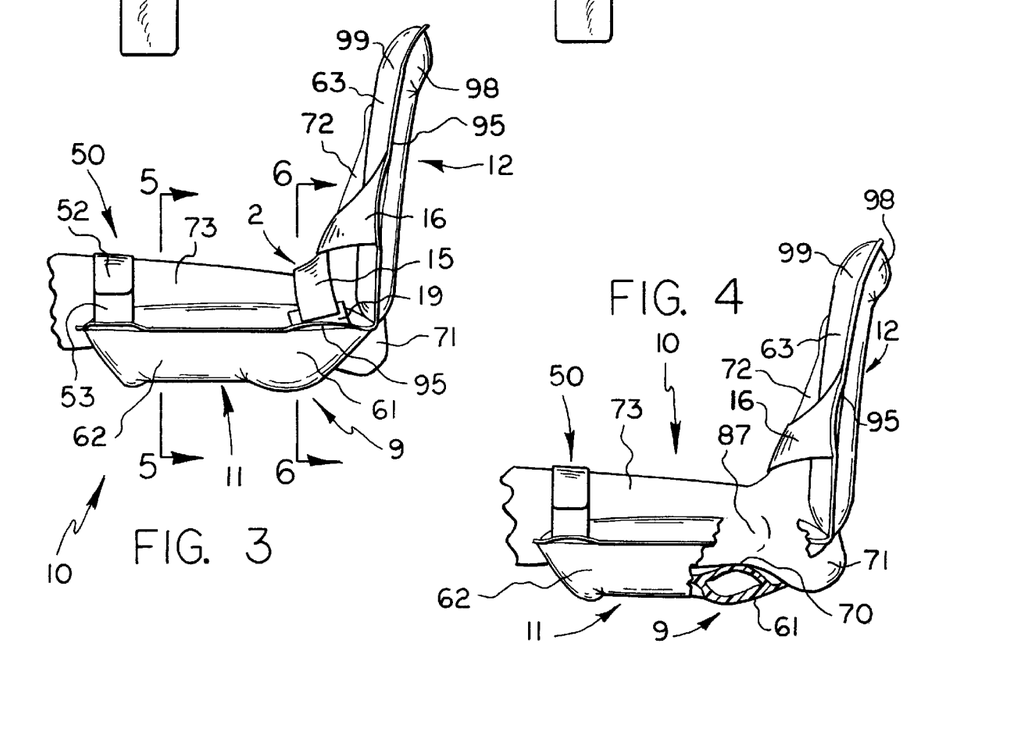
FIG. 3 is a side elevation view of the foot care device shown in FIG. 1.
FIG. 4 is a side elevation view of the foot care device shown in FIG. 1 including a partial cross-sectional view of the Achilles portion of the device.

The distal ends of elongated tabs 15 and 16 are adapted to include fastening means 22 and 23 respectively. Fastening means 22 and 23 may comprise Velcro™ pieces but other known affixing means may be employed while remaining within the scope of the present invention. The proximal ends of elongated tabs 15 and 16 include flared portions 90 and 91 which extend alongside foot section 12 in the direction of the toes of a patient such that foot section 12 and foot cushioning portion 63 will be brought into gentle but secure engagement with the foot of a patient when elongated tabs 15 and 16 are secured to short tabs 20 and 19. (Best illustrated in FIGS. 3 and 4.) As best illustrated in FIGS. 3 and 4, elongated tabs 15 and 16 are preferably affixed to foot section 12 along seam 95 on sides A and B respectively of device 10. Elongated tabs 15 and 16 may be affixed to foot section 12 of device 10 by sewing, gluing or attaching them by other known means within seam 95 of device 10. Alternatively elongated tabs 15 and 16 may be formed as an integral part of device 10 during manufacture.

Device 10 is adapted to include a heel opening 30 interposed between foot section 12 and ankle section 9. Heel opening 30 is adapted to receive the heel of a patient, the heel being inserted therethrough, thereby permitting observation of the condition of the patient's heel without removing device 10.

Ankle section 9 includes means 13 for securing foot strap means 2. Means 13 for securing foot strap means 2 includes two short tabs: side A short tab 20, and side B short tab 19. The distal ends of short tabs 20 and 19 are adapted to include on their bottom facing surfaces (best illustrated in FIG. 2) means 4 and 5 for affixing elongated tabs 15 and 16 thereto. Means 4 and 5 for affixing elongated tabs 15 and 16 are preferably Velcro™ pieces. However, other affixing means will be apparent to those skilled in the art and remain within the scope of the invention.

The proximal ends of short tab 20 and short tab 19 are affixed to ankle section 9 of device 10 by sewing, gluing or attaching by other known means to seam 95 on sides A and B respectively of device 10.

Also included in ankle section 9 is ankle support portion 61. Ankle support portion 61 is effectively separated into two halves by Achilles crevice 46. Achilles crevice 46 forms a recess in ankle support portion 61 which generally conforms to the Achilles tendon of a patient when the heel of the patient is inserted through heel opening 30. The remaining surface area of ankle support portion 61 conforms to and supports the area of the patient's foot immediately surrounding the Achilles tendon and ankle, as best illustrated in FIG. 4.

Leg section 11 includes leg strap means 50, leg cushioning portion 62 and recessed leg portion 41. Recessed leg portion 41 includes means for permitting air exchange 27. Recessed leg portion 41 lies in the central area of leg section 11. Recessed leg portion 41 is uninflated and is substantially surrounded by leg cushioning portion 62.

Leg strap means 50 comprises two elongated rectangular tabs 52 and 53. Elongated rectangular tabs 52 and 53 include affixing means 51 and 54 at their distal ends. Affixing means 51 and 54 preferably comprise Velcro™ tabs configured so as to interlock with each other when leg strap means 50 is secured around the leg of a patient (as illustrated in FIGS. 3, 4, and 7).

FIGS. 3 and 4 illustrate device 10 as it appears secured about the foot 72, ankle 87 (shown in FIG. 4) and leg 73 of a patient. As can be seen from the drawings, foot section 12 is divided into a top section 99 and a bottom section 98 by seam 95. In use, the heel 71 of a patient is positioned in heel opening 30 (shown in FIG. 1) of device 10. Foot section 12 and leg section 11 are folded toward one another until foot section 12 rests securely and comfortably against the foot 72 of the patient, while leg section 11 rests securely and comfortably against the leg 73 of the patient. Foot strap means 2 are then affixed to means 13 for securing foot strap means 2.

Figure 2:
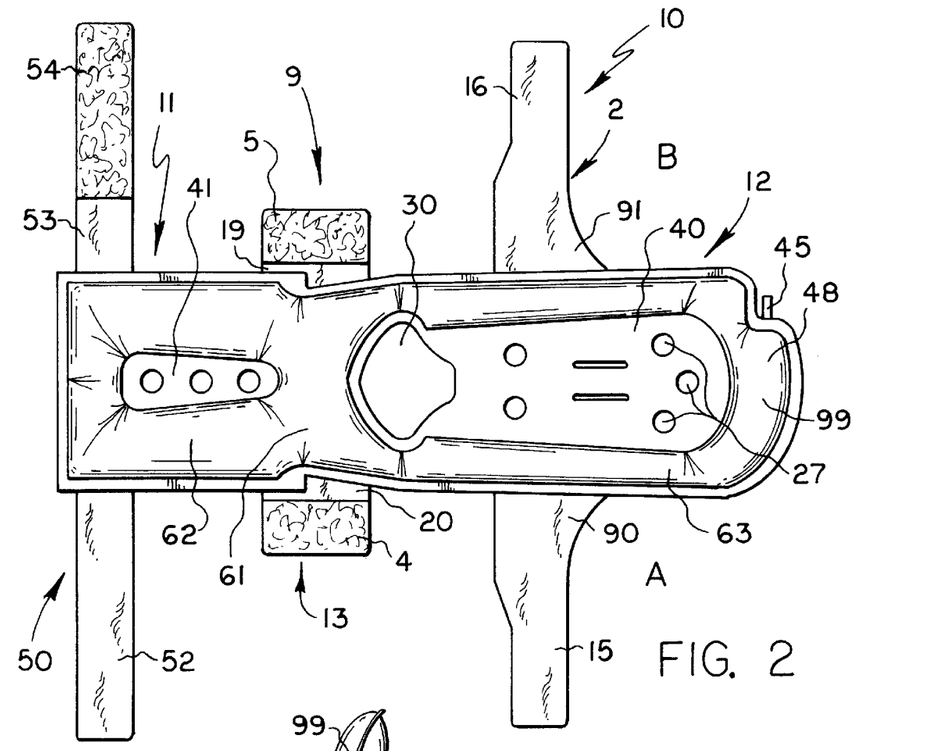
FIG. 2 is a bottom plan view of the foot care device shown in FIG. 1.
Figures 7, 9, 10:
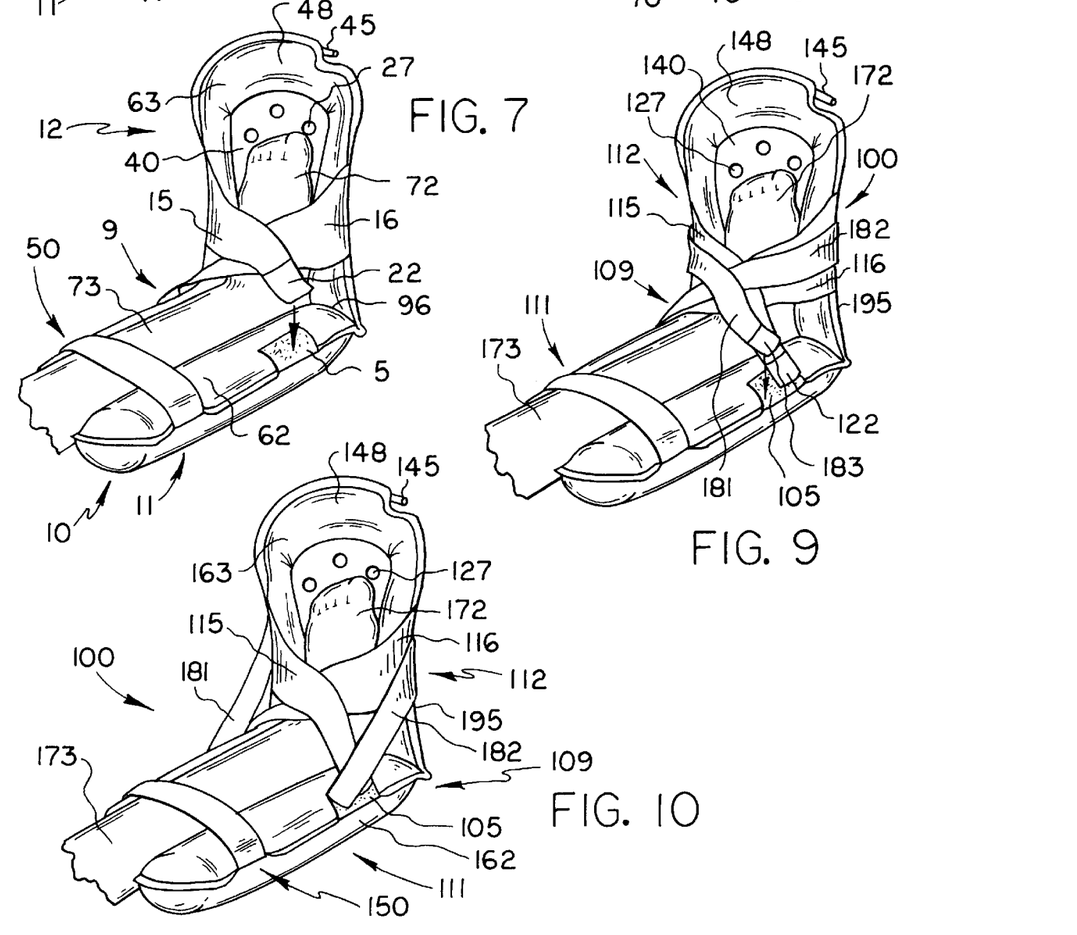
FIG. 7 is a perspective view of the foot care device of the present invention as it appears partially secured in position about the foot, Achilles tendon, and leg of a person.
FIG. 9 is a perspective view of the alternative embodiment of the present invention shown in FIG. 8, as it appears partially secured about the leg, ankle, and foot of a person.
FIG. 10 is a perspective view of the embodiment of the present invention of FIG. 8 showing an alternative method of securing the supplemental strap means.

As shown in FIG. 7, the latter is accomplished by first crossing one elongated tab, say 16, over the top of the foot 72 of the patient and toward fastening portion 4 of short tab 20, until fastening portion 23 of elongated tab 16 (best illustrated in FIG. 1) comes into contact with fastening portion 4 of short tab 20 (as best illustrated in FIG. 2). Fastening portion 23 of elongated tab 16 is then secured to fastening portion 4 of short tab 20. The action is subsequently repeated for elongated tab 15. Leg strap means 50 is secured about the calf portion of the leg 73 of the patient.

When device 10 is secured in this manner, foot cushioning portion 63, ankle support portion 61, and leg cushioning portion 62 are brought into gentle yet snug engagement with the sides of the foot 72, leg 73 and the ankle 87 of the patient. At the same time foot strap means 2, being secured about the ankle of the patient, provides further stability to the patient's ankle. In this manner the ankle of the patient is held in advantageous alignment with the foot 72 and leg 73 of the patient.

Figure 6:
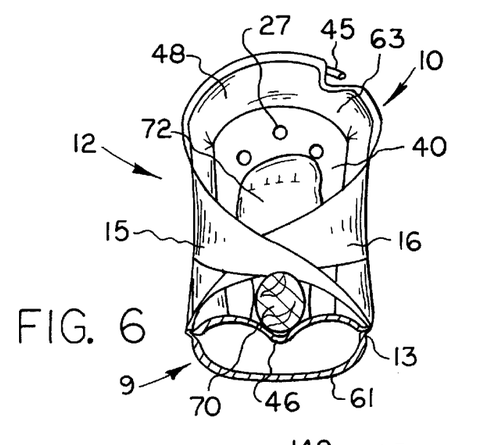
FIG. 6 is a sectional view of the foot care device shown in FIG. 3 taken along line 6—6 of FIG. 3.

FIG. 6 is a sectional view taken along lines 6—6 of FIG. 3. As can be seen in FIG. 6 Achilles crevice 46 provides pressure relief for Achilles tendon 70 of the patient. Ankle support portion 61, which is inflated with air, provides support to both sides of Achilles tendon 70, allowing the tendon itself to project into Achilles crevice 46, thereby substantially limiting the contact between Achilles tendon 70 and device 10.

Figure 5:
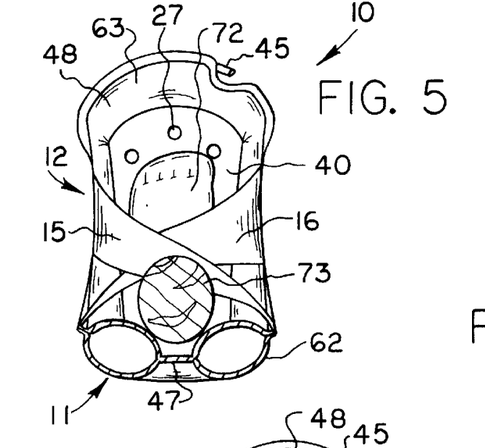
FIG. 5 is a sectional view of the foot care device shown in FIG. 3 taken along line 5—5 of FIG. 3.

FIG. 5 is a sectional view taken along lines 5—5 of FIG. 3. FIG. 5 shows leg cushioning means 62 as it supports leg 73 of a patient. Upper crevice 47 provides pressure relief for portions of leg 73 of the patient.

Figure 8:
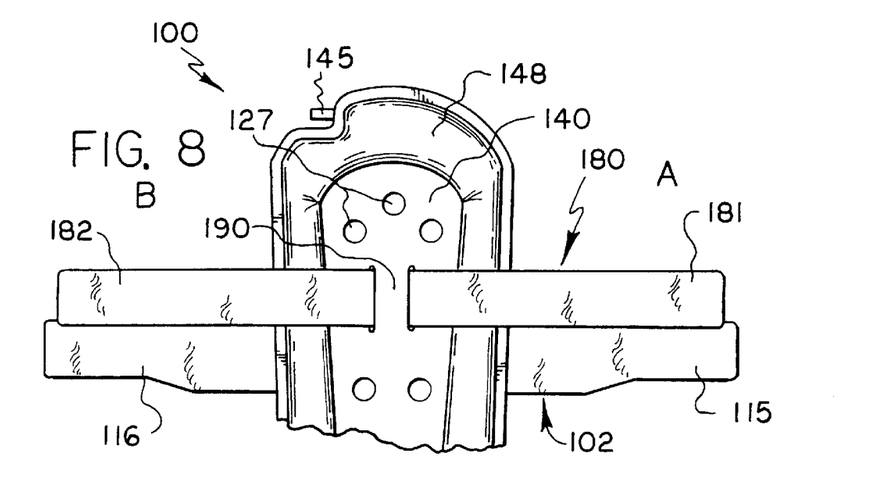
FIG. 8 is a partial bottom plan view of an alternative embodiment of the foot care device of the present invention including supplemental strap means.

FIGS. 8, 9 and 10 illustrate an alternative embodiment 100 of the device of the present invention. Device 100 is similar to device 10 and like numerals are used to indicate like parts. However, device 100 includes a supplemental strap means 180 (best illustrated in FIG. 8). Supplemental strap means 180 provides additional support to hold and immobilize a patient's foot and lower leg. Such additional support is especially useful for patients suffering from a condition known as "foot drop" in which the angle between the sole of the foot and the axis of the leg is abnormally obtuse when the muscles are relaxed.

Supplemental strap means 180 comprises two elongated strips 181 and 182 which may be affixed at their distal ends to seam 195 of foot section 112 in the same manner as previously described for elongated tabs 15 and 16 of device 10. Elongated strips 181 and 182 may be crossed over the foot 172 of a patient and affixed to short tabs (one shown) 105, thereby providing additional support to the foot 172 and ankle of a patient. Alternatively elongated strips 181 and 182 may be affixed to short tabs 104 and 105 in the manner shown in FIG. 10. That is, each elongated strip may be extended directly to the short tab located on the same side, without crossing over foot 172. This configuration supports the ankle in a manner which tends to hold the ankle in alignment with the foot and leg of the patient.

FIG. 8 is a bottom plan view of device 100 showing a preferred means for affixing elongated strips 182 and 181 to device 100. In this case supplemental strap means 180 comprises a single length of material, one end of which serves as elongated strip 181 and the other end of which serves as elongated strip 182. Supplemental strap 180 is inserted through preformed slot 190 located on the bottom of recessed foot section 140 of device 100.

Figure 11:
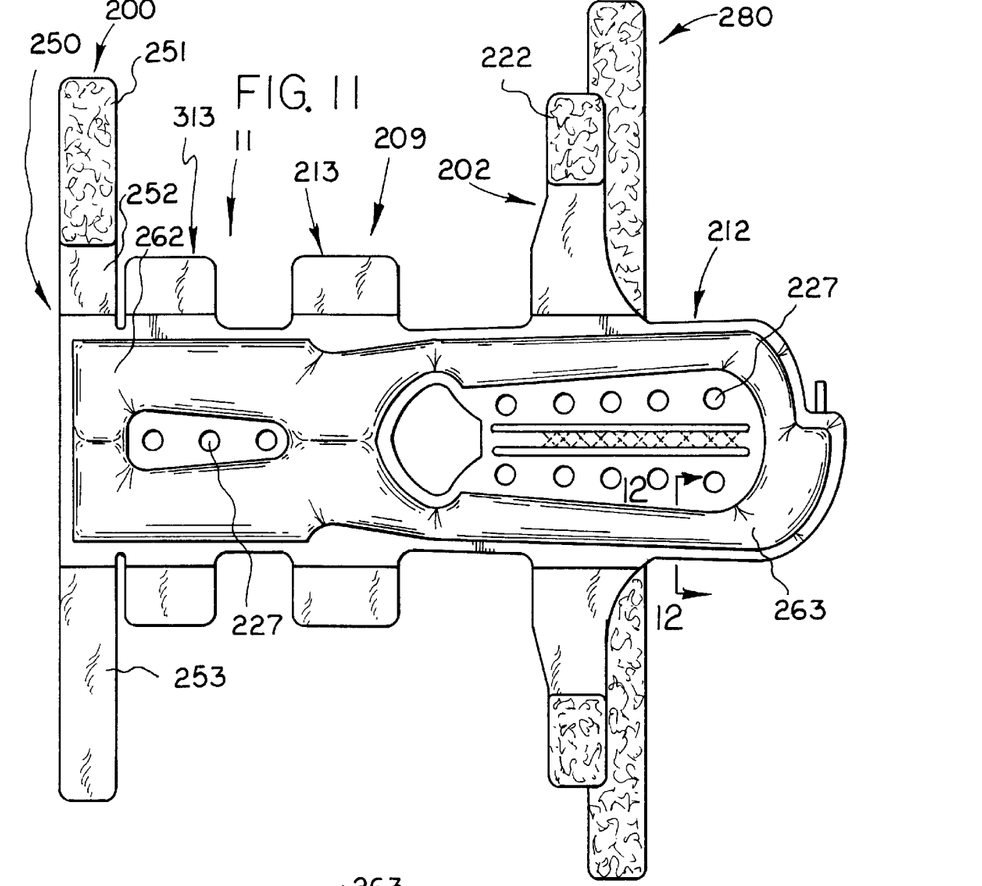
FIG. 11 is a top plan view of an alternative embodiment of the foot care device of the present invention.
Figure 12:
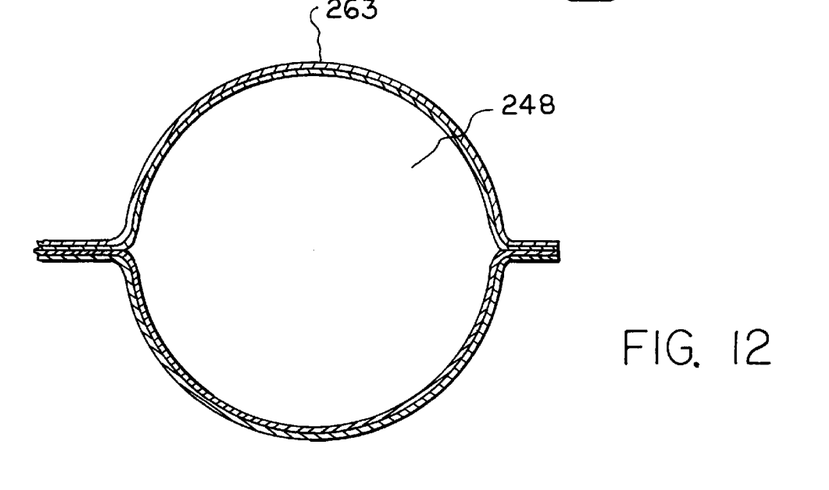
FIG. 12 is a cross sectional view of the foot care device of the present invention taken along lines 12—12.

FIG. 11 shows an alternative embodiment 200 of the foot care device of the present invention. Like reference numerals are used throughout FIG. 11 to indicate equivalent components to the embodiments shown in FIGS. 1–10. For example, in the embodiment shown in FIG. 1 a foot strap means is indicated at reference numeral 2, while in the embodiment shown in FIGS. 11, 13 and 14 equivalent foot strap means are indicated at reference numeral 202.

Device 200 has additional features which allow device 200 to more readily conform to a wider range of foot sizes than the embodiments previously described herein. Device 200 is similar to device 100 in that device 200 includes a supplemental strap means 180. However, device 200 differs from device 100 in some significant respects. First, as shown in FIG. 1, device 100 has a single means 13 for securing foot strap means 2. The same means 13 for securing foot strap means 2 may be used to secure supplemental strap means 180 of FIG. 8. While device 200 also includes means 213 for securing foot strap means 202, device 200 further includes means 313 for securing supplemental foot strap means 280. Means 213 and 313 are similar in construction to means 13 and to each other. Means 213 is located in essentially the same position as means 13 of FIG. 1, and means 313 is located between means 213 and leg strap means 250.

The addition of means 313 for securing supplemental strap means 280 provides additional flexibility as to the placement of supplemental strap means 280.

Figure 14:
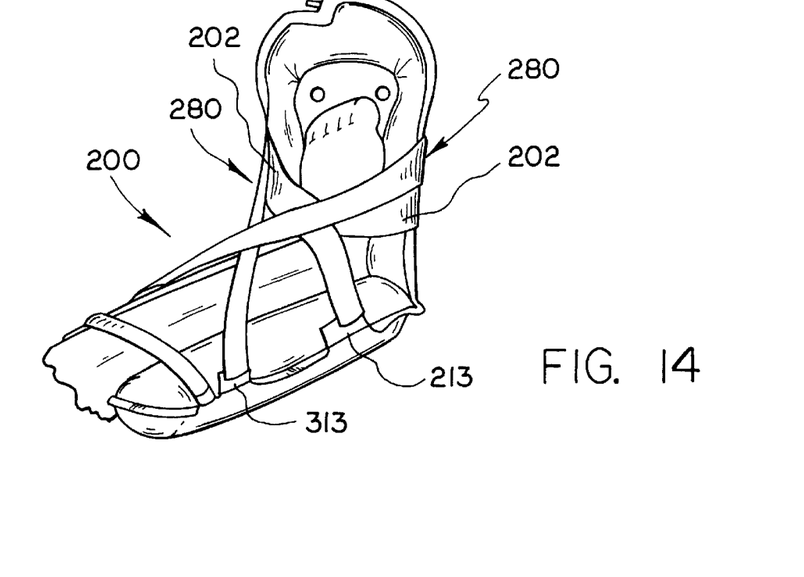
FIG. 14 is a perspective view of the foot care device shown in FIG. 11.

As shown in FIG. 14, foot strap means 202 may be secured to means 213 for securing foot strap means 202 as with the other embodiments. Supplemental foot strap means 280 may be secured to means 313 for securing supplemental strap means 280. This feature allows device 200 to be conform to a variety of foot sizes and to varying patient needs.

Figure 13:
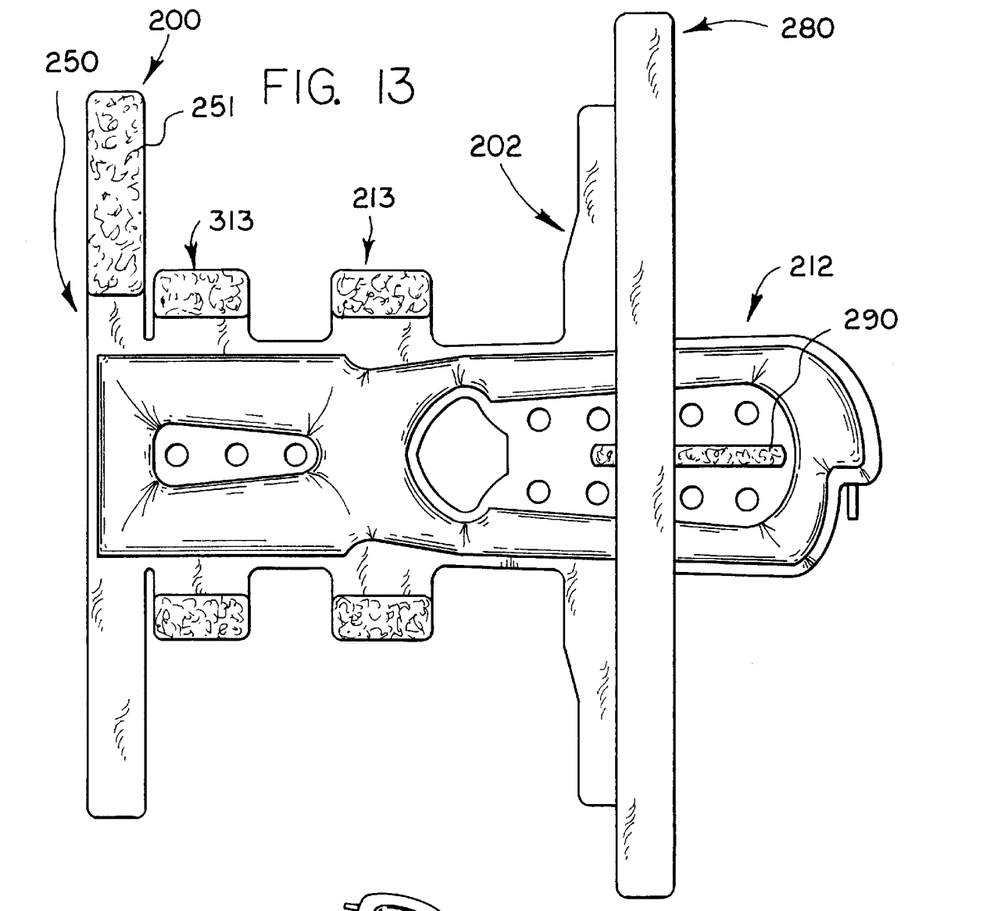
FIG. 13 is a bottom plan view of the foot care device shown in FIG. 11.

An additional feature of the embodiment shown in FIGS. 11–14 is the capability of locating supplemental strap means 280 along various positions on foot section 212 as shown in FIG. 13. Elongated fastening strip 290, which may be one of the adhering sides of a Velcro™ fastening device, extends along the bottom of foot section 212. Supplemental strap means 280 is provided with the other adhering side of the Velcro™ fastener. Accordingly, supplemental strap means 280 may be affixed in a variety of positions along elongated fastening strip 290. In that manner supplemental strap means 280 may be positioned to secure foot section 212 comfortably about the foot of a patient, in conformity with the length of the patient's foot.

Figure 15:
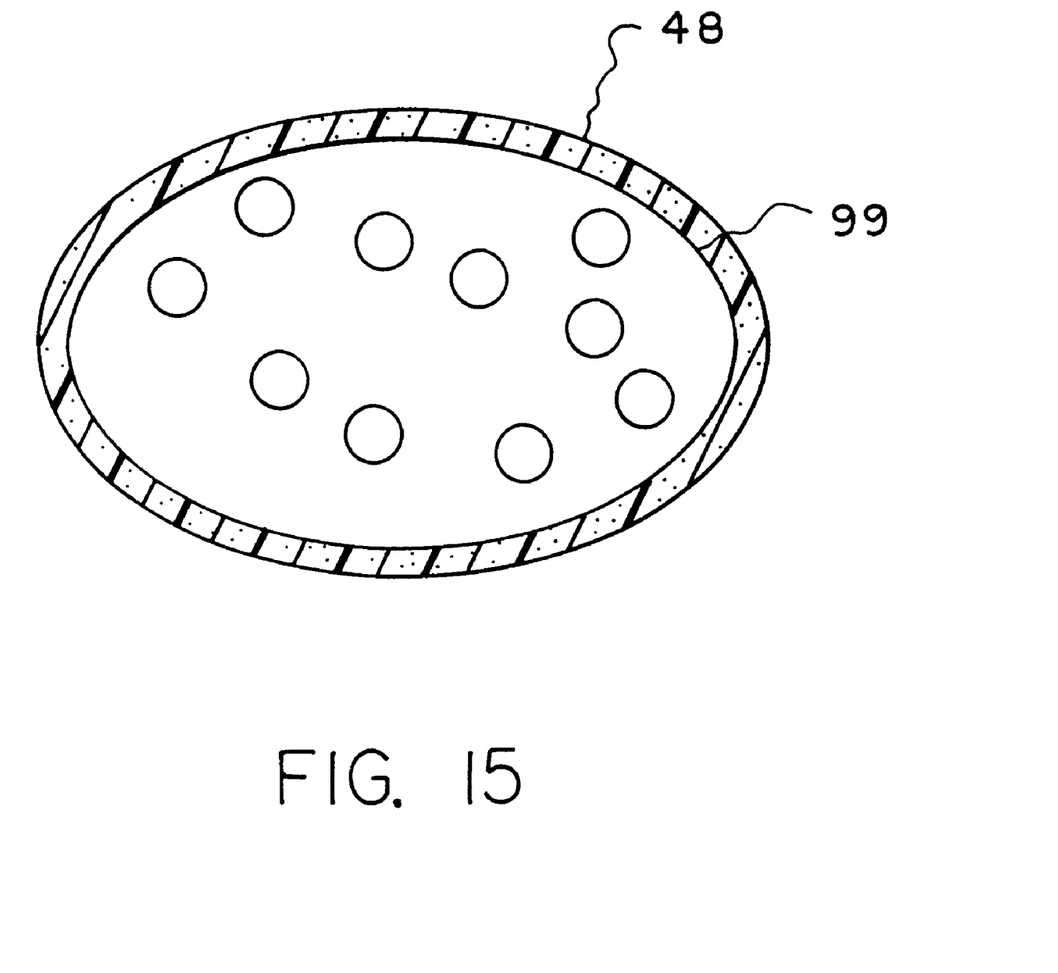
FIG. 15 is an alternative cross-sectional view of the inflatable member of FIG. 1 taken along the lines 15—15.

Alternatively as shown in FIG. 15, a sponge-like material 99 fills the interior channel means 48. The sponge material 99 when shipped is preferably flat, and when it is to be used, the consumer opens the nozzle 45 and fills the sponge material 99 with air. When filled by merely opening the nozzle 45, the sponge material 99 has the preferred air pressure. That air pressure, however can be added to or deflated to a desired alternative pressure by conventional inflation or deflation means.

Although a preferred embodiment of the invention has been disclosed in detail for illustrative purposes, it will be recognized that there are variations of modifications of the preferred embodiment, including the rearrangement of parts, which lie within the scope of the present invention.

I claim:

1. A protective and pressure normalizing device for a body extremity, the body extremity has a topside, an underside and two other sides, comprising:

an inflatable member has a lower portion that contacts at least a portion of the other sides of a lower region of the extremity, an intermediate portion that contacts at least a portion of the other sides of an intermediate region of the extremity, and an upper portion that contacts at least a portion of the other sides of an upper region of the extremity;

a heel aperture exposes the underside of the intermediate region;

a non-inflatable member has a lower portion that contacts at least a portion of the underside of the lower region, the inflatable member and heel aperture surround at least a portion of the non-inflatable member;

a means for releasably securing the device about the lower portion; and a nozzle for inflating the inflatable member to a desired internal pressure so the device engages and partially encloses in a cradling fashion the extremity and the inflating member applies a uniform interface pressure where it is applied to the extremity.

2. The device of claim 1 wherein the non-inflatable member has interspaced apertures.

3. The device of claim 1 wherein the non-inflatable member has an upper section that contacts at least a portion of the underside of the upper extremity, the upper inflatable member surrounds at least a portion of the upper non-inflatable member.

4. The device of claim 3 wherein the upper non-inflatable member has interspaced apertures.

5. The device of claim 1 wherein the inflatable chamber is a single chamber.

6. The device of claim 1 wherein the lower portion of the inflatable member is a foot cushioning portion, the intermediate portion of the inflatable member is an ankle support cushion, and the upper portion of the inflatable member is a leg cushioning portion.

7. The device of claim 1 wherein the nozzle comprises a check valve.

8. The device of claim 1 wherein the inflatable member comprises a sponge.

9. A protective and pressure normalizing device for a body extremity, the body extremity has a topside, an underside and two other sides, comprising:

a single chamber inflatable member has a lower portion that contacts at least a portion of the other sides of a lower region of the extremity, an intermediate portion that contacts at least a portion of the other sides of an intermediate region of the extremity, and an upper portion that contacts at least a portion of the other sides of an upper region of the extremity;

a heel aperture exposes the underside of the intermediate region;

a non-inflatable member has a lower portion that contacts at least a portion of the underside of the lower region, the inflatable member and heel aperture surround at least a portion of the non-inflatable member, the non-inflatable member has apertures interspaced therein;

a means for releasably securing the device about the lower portion; and a nozzle for inflating the inflatable member to a desired internal pressure so the device engages and partially encloses in a cradling fashion the extremity and the inflating member applies a uniform interface pressure where it is applied to the extremity.

10. The device of claim 9 wherein the non-inflatable member has an upper section that contacts at least a portion of the underside of the upper extremity, the upper inflatable member surrounds at least a portion of the upper non-inflatable member.

11. The device of claim 10 wherein the upper non-inflatable member has interspaced apertures.

12. The device of claim 9 wherein the lower portion of the inflatable member is a foot cushioning portion, the intermediate portion of the inflatable member is an ankle support cushion, and the upper portion of the inflatable member is a leg cushioning portion.

13. The device of claim 9 wherein the nozzle comprises a check valve.

14. The device of claim 9 wherein the inflatable member comprises a sponge.

15. A method to use a static-pressure normalizing device to a body extremity, the body extremity has a topside, an underside and two other sides, comprising the steps of:

inserting the underside of an intermediate region of the extremity into a heel aperture to expose the underside of the intermediate region;

positioning at least a portion of the underside of a lower region of the extremity upon a non-inflatable member;

placing an inflatable member upon the extremity so the inflatable member contacts at least a portion of the other sides of the lower region, at least a portion of the other sides of the intermediate region, and at least a portion of the other sides of an upper region of the extremity; and releasably securing the device about the lower portion.

16. The method of claim 15 wherein the non-inflatable member has interspaced apertures.

17. The method of claim 15 wherein the non-inflatable member has an upper section that contacts at least a portion of the underside of the upper extremity, the inflatable member surrounds at least a portion of the upper non-inflatable member.

18. The method of claim 17 wherein the upper non-inflatable member has interspaced apertures.

19. The method of claim 15 wherein the inflatable chamber is a single chamber.

20. The method of claim 15 wherein the nozzle comprises a check valve.

21. The method of claim 15 further comprising the step of inflating the inflatable member through a nozzle to a desired internal pressure, the nozzle being operable to inflate the inflatable member before the device is positioned about the lower extremity while in an underinflated state; the device engages and partially encloses in a cradling fashion the extremity and the inflating member applies a uniform interface pressure where it is applied to the extremity.

22. The method of claim 15 wherein the inflatable member comprises a sponge.

* * * * *